United States Patent [19]

Shimamune et al.

[11] Patent Number: 4,889,685

[45] Date of Patent: Dec. 26, 1989

[54] PROCESS OF PRODUCING TITANIUM COMPOSITE HAVING A COIL-SHAPED SKELETAL STRUCTURE ON THE SURFACE THEREOF

[75] Inventors: Takayuki Shimamune, Tokyo; Masashi Hosonuma, Kanagawa, both of Japan

[73] Assignee: Permelec Electrode Ltd., Kanagawa, Japan

[21] Appl. No.: 935,986

[22] Filed: Nov. 28, 1986

[30] Foreign Application Priority Data

Nov. 27, 1985 [JP] Japan ................... 60-264986

[51] Int. Cl.$^4$ .............................. B22F 7/00
[52] U.S. Cl. ............................ 419/9; 419/5; 419/23; 419/24; 419/54; 623/16
[58] Field of Search ............ 419/5, 9, 23, 24, 54; 623/16

[56] References Cited

U.S. PATENT DOCUMENTS

| | | | |
|---|---|---|---|
| 3,609,842 | 10/1971 | Shapiro | 29/157 |
| 4,038,703 | 8/1977 | Bokros | 623/1 |
| 4,122,015 | 10/1978 | Oda et al. | 210/496 |
| 4,495,664 | 1/1985 | Blanquaert | 623/23 |
| 4,644,942 | 2/1987 | Sump | 419/8 |

FOREIGN PATENT DOCUMENTS

| | | | |
|---|---|---|---|
| 3508234 | 9/1986 | Fed. Rep. of Germany | 623/16 |
| 5224938 | 2/1977 | Japan | 419/9 |
| 581936 | 11/1977 | U.S.S.R. | 623/16 |
| 1059267 | 4/1981 | United Kingdom | |
| 2142544 | 1/1985 | United Kingdom | 623/16 |

OTHER PUBLICATIONS

Great Britain Search Report.

*Primary Examiner*—Stephen J. Lechert, Jr.
*Attorney, Agent, or Firm*—Sughrue, Mion, Zinn, Macpeak & Seas

[57] ABSTRACT

A titanium composite having a coil-shaped skeletal structure on the surface, comprising a titanium or titanium alloy substrate and one or more layers of a coil-shaped skeletal titanium or titanium alloy structure that is firmly attached to the surface of said substrate and a process for producing a titanium composite having a coil-shaped skeletal structure on a surface of a titanium or titanium alloy substrate, which comprises: providing a coating composition which is a mixture of a titanium or titanium alloy powder with a binder; applying said composition in such a manner that titanium or titanium alloy coils which are to form the coil-shaped skeletal structure are firmly attached to both themselves and to the titanium or titanium alloy substrate; the heating the assembly either in vacuo or in an inert atmosphere so that the titanium or titanium alloy powder in the applied coating composition is sintered to have the coil-shaped skeletal titanium or titanium alloy structure attached firmly onto the titanium or titanium alloy substrate.

3 Claims, 1 Drawing Sheet

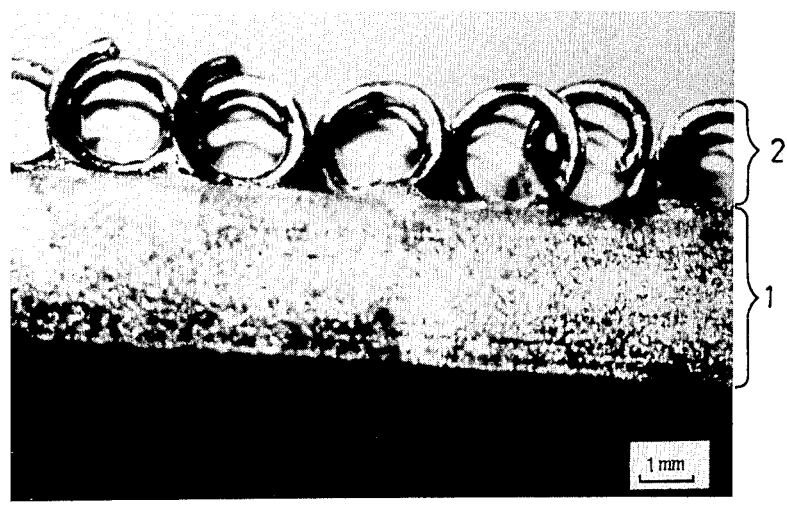

PROCESS OF PRODUCING TITANIUM COMPOSITE HAVING A COIL-SHAPED SKELETAL STRUCTURE ON THE SURFACE THEREOF

FIELD OF THE INVENTION

The present invention relates to a titanium or titanium alloy composite having on the surface thereof a coil-shaped skeletal structure of titanium or an alloy thereof. More particularly, the present invention relates to a titanium or titanium alloy composite suitable for use as an electrolytic electrode substrate, a catalyst support or a metallic material for biocompatible implants, as well as to a process for producing such composite.

BACKGROUND OF THE INVENTION

Being known as a metallic material having superior mechanical strength and chemical durability, titanium has long been used in various fields. For instance, titanium-based electrodes are exclusively used in modern electrolytic equipment for producing chlorine and sodium hydroxide by electrolysis of aqueous sodium chloride. The titanium-based electrodes comprise a titanium substrate coated with an electrode active material and, in order to ensure higher electrode performance as manifested by prolonged service life and lower overpotential, the substrate desirably has an adequately large surface area and strong adhesion to the coating. To this end, it has been proposed to roughen the surface of the titanium substrate by either blasting or etching but the increase in surface area can be achieved only with respect to a shallow surface layer and the anchor effect attained is not strong enough to provide firm adhesion to the coating material.

Porous titanium materials which are generally spongy or fibrous are known (see, for example, Japanese Patent Application (OPI) No. 8416/80 (the term "OPI" means an unexamined published application)) but they are not suitable for use in applications where high mechanical strength is required.

There are many metallic members that require high physical and chemical strength, large surface areas and a high capacity for anchoring the coating material: they include, in addition to the electrode substrate described above, carrier supports for use in chemical reactors and metallic materials for biocompatible implants such as artificial bones. However, no titanium-based materials have been developed to date that satisfy all of the requirements for use in these applications.

SUMMARY OF THE INVENTION

One object, therefore, of the present invention is to provide a titanium or titanium alloy composite having improved physical and chemical strength, which has a large surface area and exhibits a great capability of anchoring a coating material.

Another object of the present invention is to provide a process that is capable of readily producing a titanium or titanium alloy composite having such superior characteristics.

In accordance with the present invention, the aforementioned objects are attained by providing a titanium composite having a coil-shaped skeletal structure on the surface, comprising one or more layers of a coil-shaped skeletal structure of titanium or an alloy thereof that adheres strongly onto the surface of a titanium or titanium alloy substrate.

The present invention also provides a process for producing a titanium composite having a coil-shaped skeletal structure on a surface of a titanium or titanium alloy substrate, which comprises: providing a coating composition which is a mixture of a titanium or titanium alloy powder with a binder; applying said composition in such a manner that titanium or titanium alloy coils which are to form the coil-shaped skeletal structure are firmly attached to both themselves and to the titanium or titanium alloy substrate; the heating the assembly either in vacuo or in an inert atmosphere so that the titanium or titanium alloy powder in the applied coating composition is sintered to have the coil-shaped skeletal titanium or titanium alloy structure attached firmly onto the titanium or titanium alloy substrate.

BRIEF DESCRIPTION OF THE DRAWING

The FIGURE is a micrograph showing a cross section of a titanium composite sample having a coil-shaped skeletal structure on the surface in accordance with the present invention.

DETAILED DESCRIPTION OF THE INVENTION

In the present invention, elemental titanium is typically used as a substrate material but, if a specific use requires, titanium alloys containing other metals such as Ta, Nb, platinum group metals, Al and V may be employed. The substrate shaped into a plate, rod or any other appropriate form is preferably subjected to a surface-cleaning treatment by washing, for example, with water, acids, ultrasonic waves or steam. If desired, the clean surface of the substrate may be roughened or activated by combinations of suitable techniques well known to those skilled in the art such as etching and blasting. Grooves that match the outer configuration of a coil-shaped member that is to be fixed to the titanium substrate may be provided in the surface of the latter by suitable working such as fluting for the purpose of allowing the coil-shaped member to join with the substrate over a sufficiently large area to ensure stronger adhesion of said member to the substrate.

The surface-treated titanium substrate is then provided with a firmly adhering coil-shaped skeletal structure of titanium or an alloy thereof by the following procedure: first, a titanium or titanium alloy wire is wound onto a bobbin having a circular or polygonal cross section so as to form a coil having a cross section corresponding to that of the bobbin. In order to prevent turns of a coil from becoming entangled with those of an adjacent coil, it is preferable that the gap between adjacent turns of each coil is not greater than the diameter of the titanium wire. As the coil material, a titanium wire and a titanium alloy as used for the substrate may be used. The coils are preferably subjected to the surface-cleaning treatment as described with respect to the substrate.

Subsequently, a layer of titanium coils thus prepared is placed on the titanium substrate, and a paste of a mixture containing a titanium or titanium alloy powder and a binder is applied to the matting surfaces of adjacent coils and those of each coil and the substrate such that the coils adhere both to themselves and to the substrate to form a coil-shaped skeletal structure on the surface of the titanium substrate. The assembly is then heated either in vacuo or in an inert gas to dry and sinter the mixture of a titanium or titanium alloy powder and a binder, whereby a titanium composite having a strongly adhering coil-shaped skeletal structure on the surface can be obtained.

The adhering coils may be provided on all or part of the substrate surface. If desired, two or more layers of coils may be adhered to the substrate. The mixture which is applied for the purpose of allowing adjacent coils to adhere both to themselves and to the substrate is prepared by adding a binder such as CMC (carboxymethyl cellulose) or collodion, or water or an organic solvent to a titanium or titanium alloy powder so as to form a slurry. The resulting coating composition in a paste form is then applied to the matting surfaces by suitable means known to those skilled in the art such as brushing. The titanium or titanium alloy powder used in the mixture typically has a particle size ranging from several microns to about 300 microns. Also usable is a powder of a titanium compound such as hydrogenated titanium which readily undergoes thermal decomposition into metallic titanium.

Heating of the titanium substrate having a coilshaped skeletal structure on the surface is preferably conducted at between 900° and 1,400° C. in order to allow the titanium powder to be firmly joined to the coils and substrate through metal fusion at the interface. A temperature within this range may be maintained for a period of from about 30 minutes to about 5 hours.

The Figure is a micrograph (magnification: about 8x) showing a cross section of a titanium composite sample produced in accordance with the present invention.

There are other methods for allowing the titanium coils to adhere firmly to the titanium substrate and they include various welding techniques such as TIG welding, MIG welding, electron beam welding, resistance welding, ultrasonic welding and diffusion welding. Brazing is another method that can be effectively employed for attaining the same purpose.

The advantages of the present invention are hereunder described in greater detail with reference to the following examples which will in no way limit the scope of the invention.

Unless otherwise specified, all percents, ratios, etc. are by weight.

EXAMPLE 1

Titanium coils with a circular cross section were prepared by winding wires of titanium (Type 2, defined in Japanese Industrial Standard (JIS)) with a diameter of 0.5 mm onto cylindrical bobbins (diameter: 1.0 mm) at a pitch of 0.5 mm. A rolled plate of titanium (Type 2, JIS) measuring 25 mm'15 mm×3 mm and the coils were cleaned with ultrasonic waves in acetone. Thereafter, the surface of the Ti plate was activated by being immersed in boiling 20% HCl for 5 minutes.

A titanium powder having a particle size of 44 μm or smaller was blended with a small amount of a 1.5% aqueous solution of CMC to make a paste. The paste was applied onto the surface of the Ti plate and a layer of closely arranged Ti coils was securely attached to the Ti plate. The assembly was dried at 60° C. in an argon stream from which oxygen and moisture had been fully removed. Thereafter, the assembly was heated at 1,050° C. for 3 hours so as to sinter the matting surfaces of the coils and the Ti plate. As a result, a titanium composite having a coil-shaped skeletal structure on the surface was obtained. As the Figure shows, this composite had the coils 2 strongly adhering onto the Ti substrate 1.

An anode was fabricated by pyrolytic coating of an electrode active material (i.e., iridium oxide) on the substrate made of the Ti composite that was prepared in accordance with the present invention. The anode was used in electrolytic evolution of oxygen in an aqueous solution of sulfuric acid (150 g/l) at 60° C. and at a current density of 150 A/dm$^2$. The measured anode potential was 40 mV lower than the value occurring at a conventional anode which employed as a substrate a smooth-surfaced Ti plate having no coil-shaped skeletal structure on the surface. This showed that the titanium composite having a coil-shaped skeletal structure on the surface in accordance with the present invention would provide an electrode substrate having an effective surface area about 4.5 times as large as that of the conventional smooth-surfaced titanium plate.

EXAMPLE 2

Coils were prepared by winding wires of titanium (Type 2, JIS) with a diameter of 0.3 mm onto bobbins (diameter: 0.5 mm) at a pitch of 0.2 mm. In a separate step, a cylindrical casting of 6A1-4V-Ti alloy (55 mm$^\phi$×50 mm$^L$) was provided on the side wall with spiral grooves of a semicircular cross section that were formed with a fluting tool. The grooved cylinder and the coils were cleaned with ultrasonic waves in acetone. Thereafter, the surface of the cylinder was activated by being immersed in 1.5% H$_2$SO$_4$ at 80° C. for 30 minutes.

A hydrogenated titanium powder having a particle size of 37 μm or smaller was blended with a 1.5% aqueous solution of CMC to make a paste. A portion of the paste was applied to the side of the cylindrical substrate and a layer of the coils were temporarily attached to the substrate along the spiral grooves. The remainder of the paste was applied to both the substrate and the coils and another layer of coils was securely attached to the first layer of coils. The assembly was dried at 60° C. in an argon stream from which oxygen and moisture had been fully removed. Thereafter, the assembly was heated at 1,100° C. for 2 hours so as to sinter the matting surfaces between the stacked coil layers and between the coils and the substrate. As a result, a titanium composite was obtained wherein the coils adhered strongly onto the surface of the substrate.

The resulting titanium composite with a coil-shaped skeletal structure on the surface had a surface area equivalent to a porous titanium body possessed of pores ranging in size from 300 μm to 500 μm. As is well known, a porous body for use as a biocompatible implant is required to have a pore size of 150 μm or more so that it will admit the entrance of bone cells. The titanium composite prepared in accordance with the present invention has sufficient levels of porosity and Ti wire tenacity and exhibits a strong anchor effect so that it can be used as a very effective metallic material for biocompatible implants.

The titanium composite prepared in accordance with the present invention has a coil-shaped skeletal titanium structure that adheres strongly onto a titanium substrate and the composite exhibits improved physical and chemical strength, has a large surface area and displays a great capability of anchoring a coating material. This composite is highly useful as an electrode substrate, a catalyst support or as a metallic material for biocompatible implants. In accordance with the present invention, the coil-shaped skeletal structure can be firmly attached to the titanium substrate by sintering, welding or bracing and this provides a simple way to attain a titanium composite having a desired thickness and porosity.

While the invention has been described in detail and with reference to specific embodiments thereof, it will be apparent to one skilled in the art that various changes and modifications can be made therein without departing from the spirit and scope thereof.

What is claimed is:

1. A process for producing a titanium composite having a coil-shaped skeletal structure on a surface of a titanium or titanium alloy substrate, which comprises:

providing a coating composition which is a mixture of a titanium or titanium alloy powder with a binder;

providing titanium or titanium alloy coils on the surface of a titanium or titanium alloy substrate;

applying said coating composition in such a manner that said titanium or titanium alloy coils which are to form the coil-shaped skeletal structure are securely attached to both themselves and to the titanium or titanium alloy substrate; then heating the assembly either in vacuo or in an inert atmosphere so that the titanium or titanium alloy powder in the applied coating composition is sintered to have the coil-shaped skeletal titanium or titanium alloy structure attached firmly onto the titanium or titanium alloy substrate.

2. A process as in claim 1, wherein the heating of the assembly is achieved at a temperature of between 900° and 1,400° C.

3. A process as in claim 1, wherein the titanium or titanium alloy substrate is grooved in the surface.

* * * * *